United States Patent
Chadwick et al.

(10) Patent No.: US 7,092,083 B2
(45) Date of Patent: Aug. 15, 2006

(54) APPARATUS FOR PRESENTING A SAMPLE OF MATERIAL FOR ANALYSIS

(75) Inventors: Bruce Leonard Chadwick, Glen Iris (AU); Douglas George Body, South Yarra (AU); Trevor David Thomson, Hawthorne (AU)

(73) Assignee: XRF Scientific Limited, Victoria (AU)

( * ) Notice: Subject to any disclaimer, the term of this patent is extended or adjusted under 35 U.S.C. 154(b) by 331 days.

(21) Appl. No.: 10/488,304

(22) PCT Filed: Aug. 29, 2002

(86) PCT No.: PCT/AU02/01181

§ 371 (c)(1),
(2), (4) Date: Mar. 1, 2004

(87) PCT Pub. No.: WO03/021238

PCT Pub. Date: Mar. 13, 2003

(65) Prior Publication Data

US 2004/0239925 A1    Dec. 2, 2004

(30) Foreign Application Priority Data

Sep. 5, 2001 (AU) .................................. PR7498

(51) Int. Cl.
*G01N 21/01* (2006.01)
*G01J 3/30* (2006.01)

(52) U.S. Cl. ...................................... 356/244; 356/318
(58) Field of Classification Search ................ 356/244, 356/246, 317, 318, 343
See application file for complete search history.

(56) References Cited

U.S. PATENT DOCUMENTS 4,265,535 A * 5/1981 Pitt .............................. 356/70
4,534,651 A * 8/1985 Minikane ..................... 356/440

FOREIGN PATENT DOCUMENTS

JP    62-012844    1/1987

* cited by examiner

*Primary Examiner*—Gregory J. Toatley
*Assistant Examiner*—Marissa J Detschel
(74) *Attorney, Agent, or Firm*—Paul and Paul

(57) ABSTRACT

An apparatus for presenting a sample of material for analysis by a laser-based analyzer comprises a chamber, a first window for admitting laser radiation to the chamber, sample presentation means for presenting a sample such that said laser radiation can impinge upon the sample, and a plurality of second windows (76,78,80,82) for receiving radiation emitted from the sample, said plurality of second windows (76,78, 80,82) adapted to pass radiation emitted from the sample to a plurality of detector means. The apparatus further includes a gas inlet (98) and a gas outlet (100) to enable the atmosphere inside the chamber (52) to be controlled.

22 Claims, 5 Drawing Sheets

APPARATUS FOR PRESENTING A SAMPLE OF MATERIAL FOR ANALYSIS

FIELD OF THE INVENTION

The present invention relates to an apparatus for presenting a sample of material for analysis. The apparatus is especially suitable for presenting a sample of material for analysis by a laser-based analyser.

BACKGROUND OF THE INVENTION

International patent application no. PCT/AU99/00713 in the name of the present applicants describes a laser-based analyser. This analyser can be used to analyse solid, liquid or even gaseous materials. However, the analyser is most suitably used for analysing solid materials, such as coal.

In the analyser described in international patent application no. PCT/AU99/00713, laser radiation is focussed onto a sample, which causes the sample to emit light. The emitted light is detected by a plurality of detectors. The plurality of detectors detects information from specific parts of the spectral region and forwards that information to respective data collecting means.

An embodiment of the analyser described in international patent application no PCT/AU99/00713 is described with reference to FIG. 1 attached hereto.

In the apparatus shown in FIG. 1, a laser 10, which may be a 1064 mm ND:YAG laser, emits pulses of laser light that are focussed by an optical system 12 onto a material to be analysed 14. In the small region of the laser spot focused on the material 14, the laser power density produces rapid heating and ionisation of a small sample of the material. Light is emitted from the vaporised and ionised material containing spectral information on the material involved. The light emitted from the vaporised and ionised material is schematically represented at 16 and this emitted light is detected by a plurality of detection means 20, 22, 24. The apparatus shown in FIG. 1 has three detection means but it will be appreciated that a lesser or greater number of detection means may be utilised. It is envisaged that a greater number of detection means may be utilised if especially high resolution is required. Detection means 20 comprises a spectrometer 26 that is adjusted to a part of the spectrum of the spectral emissions emanating from material 14. Detection means 20 also includes a CCD detector 21 which suitably comprises a readily available commercial CCD detector. The CCD detector 21 may comprise a 12–16-bit detector.

Similarly, detection means 22 comprises a spectrometer 30 and a CCD detector 32. Detection means 24 also comprises a spectrometer 34 and CCD detector 36.

The CCD detectors 21, 32, 36 detect information from the specific spectral region provided by their associated spectrometers. The CCD detectors then pass the detected information to respective dedicated data acquisition means 38, 40, 42. The data acquisition means may include analog-to-digital conversion boards/circuitry. The computer 44 also includes control means 46 to control the operation of the laser 10 and the plurality of the detection means 20, 22, 24.

In use of the apparatus shown in FIG. 1, the control means 46 sends a control signal to laser 10 which causes the laser to emit a pulse of laser light. The pulse of laser light 10 is focused onto the surface of material 14 which causes vaporisation and ionisation of a small part of the material 14.

Shortly after the control signal causes a pulse of laser light 10 to be emitted by the laser, the control means 46 sends control signals to the detection means 20, 22, 24 which turns on those detection means. It is preferred that there is a slight delay between firing of the laser and initialisation of operation of the spectrometers in order to ensure that the CCD detectors do not detect the pulse of laser light and only detect the emitted spectra. This control signal causes the spectrometers 26, 30, 34 to collect light from the relevant spectral region for a predetermined period of time and to enable the CCD detectors 21, 32, 36 to detect that light. Each of spectrometers 26, 30, 34 collect light from particular regions of the emission spectrum. The particular regions may be discrete, separate regions of the spectrum, or there may be some overlap between the spectral region collected by one of the spectrometers and the spectral region collected by another of the spectrometers. Whilst the detection means 20, 22, 24 are collecting and detecting the light from the emitted spectral region from the sample 14, the CCD detectors are also forwarding information to the respective data acquisition means 38, 40, 42. The CCD detectors are formed from individual areas of light sensitive material (usually silicon) known as pixels. Each pixel converts the light intensity to an electric change or current which is then digitised by the data acquisition means. The use of separate data acquisition means for each detection means enables rapid collection of large amounts of data and this in turn allows the rapid analysis of the material to take place at high spectral resolution.

The data collected by the data acquisition means 38, 40, 42 is then analysed by the computer to determine the elements of species present in the material and also to determine the relative amounts of each of those elements or species. The amount of each element or species in the material may be determined by integrating the area under the spectral line at a wavelength that is characteristic of the spectral emission of a given element or species and comparing that area with the area under the same spectral line obtained from a material having a known content of that particular element or species.

SUMMARY OF THE INVENTION

It is an object of the present invention to provide an apparatus for presenting a sample of material for analysis.

In the first embodiment, the present invention provides an apparatus for presenting a sample of material for analysis by a laser-based analyser comprising a chamber, a first window for admitting laser radiation to the chamber, sample presentation means for presenting a sample such that said laser radiation can impinge upon the sample, and a plurality of second windows for receiving radiation emitted from the sample, said plurality of second windows adapted to pass radiation emitted from the sample to a plurality of detector means.

In one embodiment, the chamber has one or more walls to define an interior thereof. The first window and the plurality of second windows are preferably formed in the walls of the chamber.

Preferably, the sample presentation means presents the sample to the interior of the chamber.

The sample presentation means is preferably removably secured to one or more walls of the chamber. More preferably, a wall of the chamber has an aperture therein and the sample presentation means positions the sample over, in or through, the aperture such that laser radiation can pass through the first window and impinge upon the sample.

It is especially preferred that the sample presentation means forms a gas-tight seal when the sample presentation means is secured to the wall of the chamber. The gas-tight seal may be achieved, for example, by providing a sealing gasket on the outside of the wall to which the sample presentation means is removably secured.

In one embodiment, the first window comprises or includes a lens to enable laser radiation to be focussed onto the sample. The position of the lens may suitably be adjustable to allow the focussing point for the laser radiation to be adjusted. The lens is suitably placed in an adjustable mount to allow focussing onto the surface of the sample being analysed. This is a useful feature that enables a number of separate samples to be sequentially analysed by the analyser without requiring exact placement of each sample onto an identical location on the sample presentation means.

Alternatively, and more preferably, the sample presentation means is moved during irradiation of the sample by the laser so that the sample is scanned across the laser beam. This assists in reducing any analysis errors associated with sample heterogeneity.

It is also preferred that the plurality of second windows include or comprise lenses for collecting and focusing emitted light from the sample. Similarly to the first lens, the plurality of second lenses may also be adjustable to enable their focal point to be adjusted.

The apparatus may further include laser holding means for holding a laser. Preferably, the laser holding means aligns an output of the laser with the first window. Preferably, the laser holding means releasably holds the laser.

In other embodiments, the laser holding means may be separate to the apparatus, such as a stand-alone stand.

The apparatus may also further comprise a plurality of detector holding means for holding a plurality of detectors. The detector holding means preferably releasably hold the detectors. The detector holding means preferably align the detectors with respective second windows.

Preferably, the detector holding means align the detectors such that the detectors detect emitted light from a position in front of the sample. Preferably, the detector holding means aligns the detectors such that the detectors detect emitted light from a position that is 1 to 5 millimeters in front of the sample, more preferably about 2 millimeters in front of the sample.

In another embodiment, the second windows comprise or include lenses and the lenses are focused to receive emitted light from a position in front of the sample. Preferably the lenses in or part of the second windows are focussed to receive emitted light from a position that is 1 to 5 millimeters in front of the sample, more preferably about 2 millimeters in front of the sample.

The apparatus may further comprise atmosphere control means for controlling the atmosphere inside the chamber. The atmosphere control means may comprise a gas inlet into the chamber for admitting gas into the chamber and a gas outlet from the chamber for removing gas from the chamber. This enables a purge or a buffer gas to flow into the chamber. Alternatively, the chamber may have a vacuum port for applying a vacuum to the chamber. It will be appreciated that, in embodiments where the apparatus includes a gas inlet and a gas outlet, that a vacuum line may be attached to either the gas inlet or the gas outlet if it is designed to apply a vacuum to the chamber.

The apparatus may further comprise dust collection means for collecting dust from the sample. The dust collection means is preferably removable. The dust collection means may suitably comprise a sliding tray. Preferably, the dust collection means is in sealing engagement with the chamber when the dust collection means is in a closed position. The dust collection means most suitably is positioned in a lower part of the chamber.

In a further preferred embodiment, the apparatus comprises safety interlock means for preventing firing of the laser if part of the apparatus is open. In one embodiment, the safety interlock means comprises an interlock associated with the sample presentation means to prevent firing of the laser if the sample presentation means is not closed. In another embodiment, the safety interlock means comprises an interlock associated with the dust collection means to prevent firing of the laser when the dust collection means is not fully closed. The interlock means preferably comprises electrical interlock means.

In another embodiment, the plurality of second windows enable optical fibres to receive emitted light from the sample. In this embodiment, the apparatus may also include optical fibre holding means for holding the optical fibres in a desired position. In this embodiment, the optical fibres are used to image the light emission from the sample.

When using optic fibre to transmit the emitted light observed through the plurality of second windows, the aperture of the fibre restricts the viewing zone to the region of maximum light emission (about 2 mm in front of the sample, typically). This is a convenient way of ensuring only the light emission of interest is passed onto the spectrometers, thus resulting in superior signal-to-noise ratio.

DETAILED DESCRIPTION OF THE EMBODIMENTS

It will be appreciated that the drawings shown in FIGS. 2 to 6 show a preferred embodiment of the present invention and have been provided in order to illustrate that preferred embodiment of the invention. It is to be understood that the invention should not be considered to be limited to the embodiments as shown in FIGS. 2 to 6.

Figure 1:
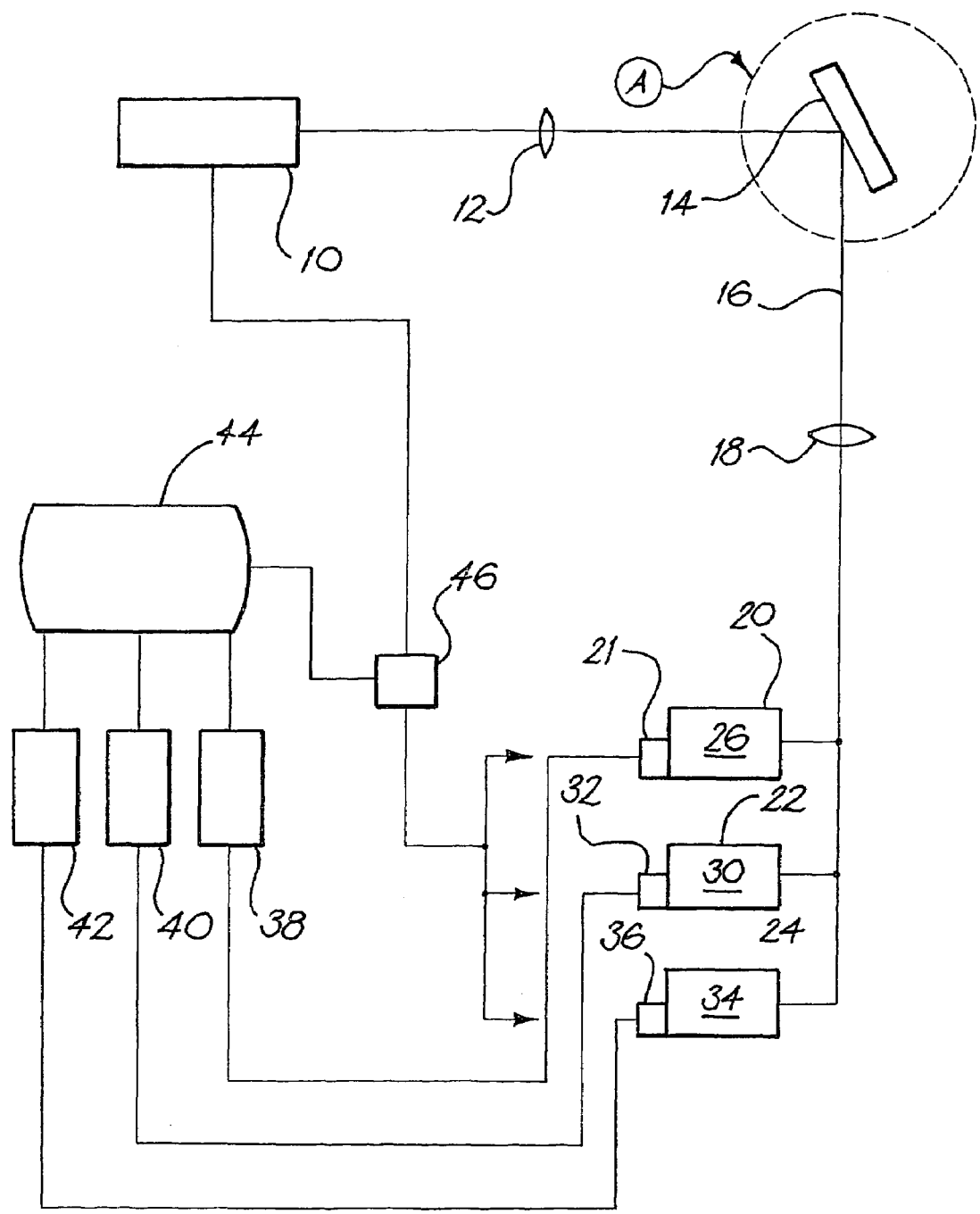
FIG. 1 shows a schematic diagram of the analyser described in the present applicant's international patent application no. PCT/AU99/00713.
Figure 2:
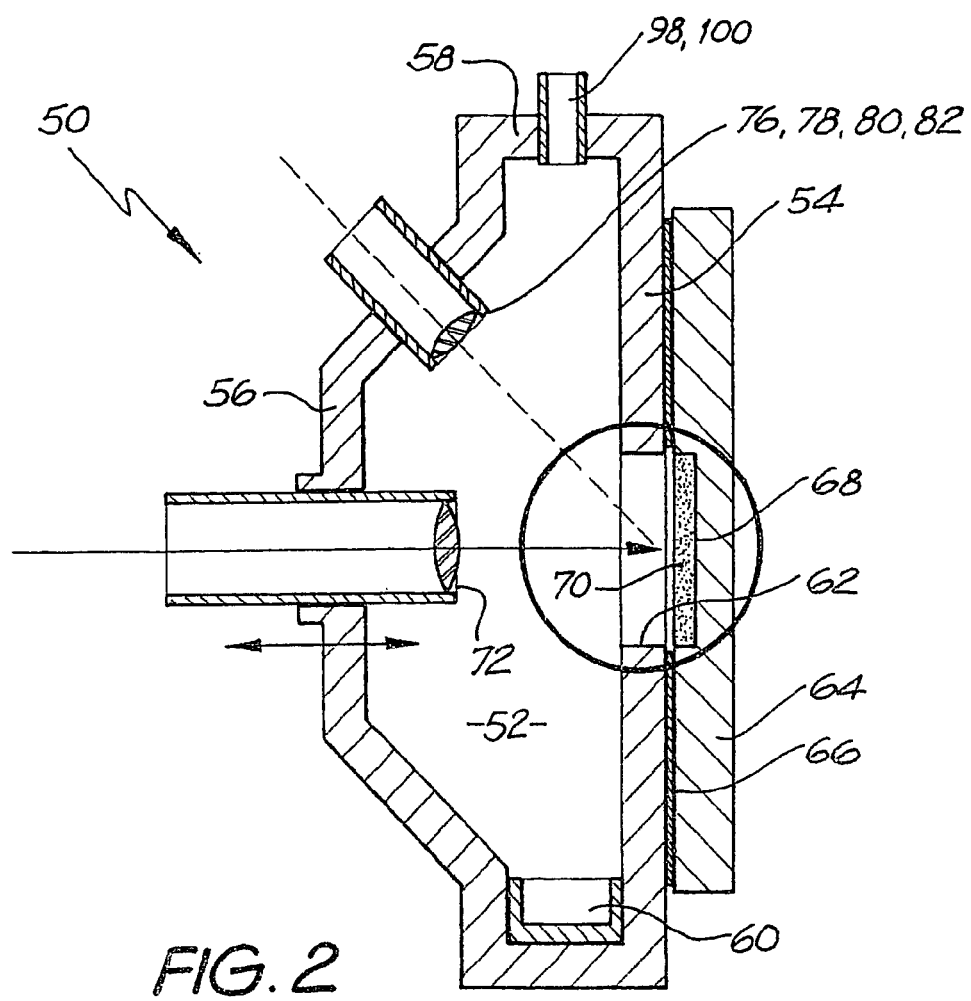
FIG. 2 shows a schematic side view, in cross section, of an apparatus for presenting a sample of material for analysis in accordance with the present invention.
Figure 3:
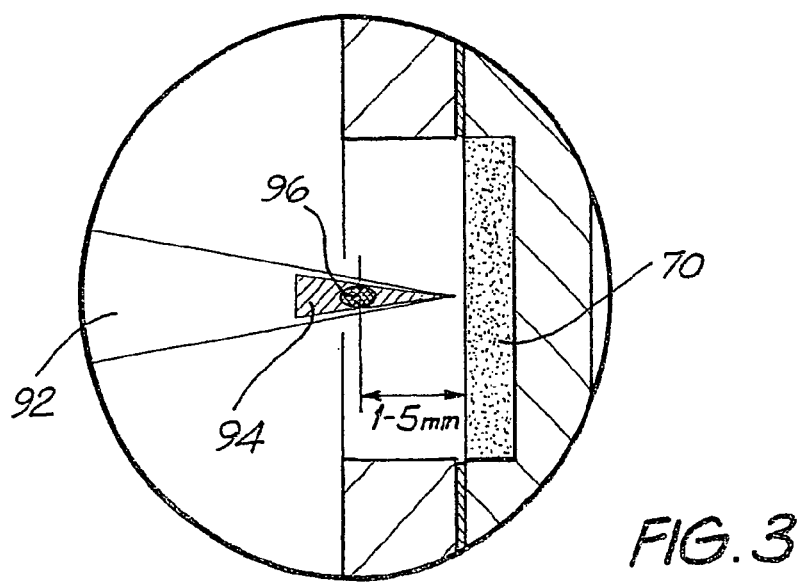
FIG. 3 is a schematic diagram of the emission zone of light emitted from the sample and the focal area of the detectors.
Figure 4:
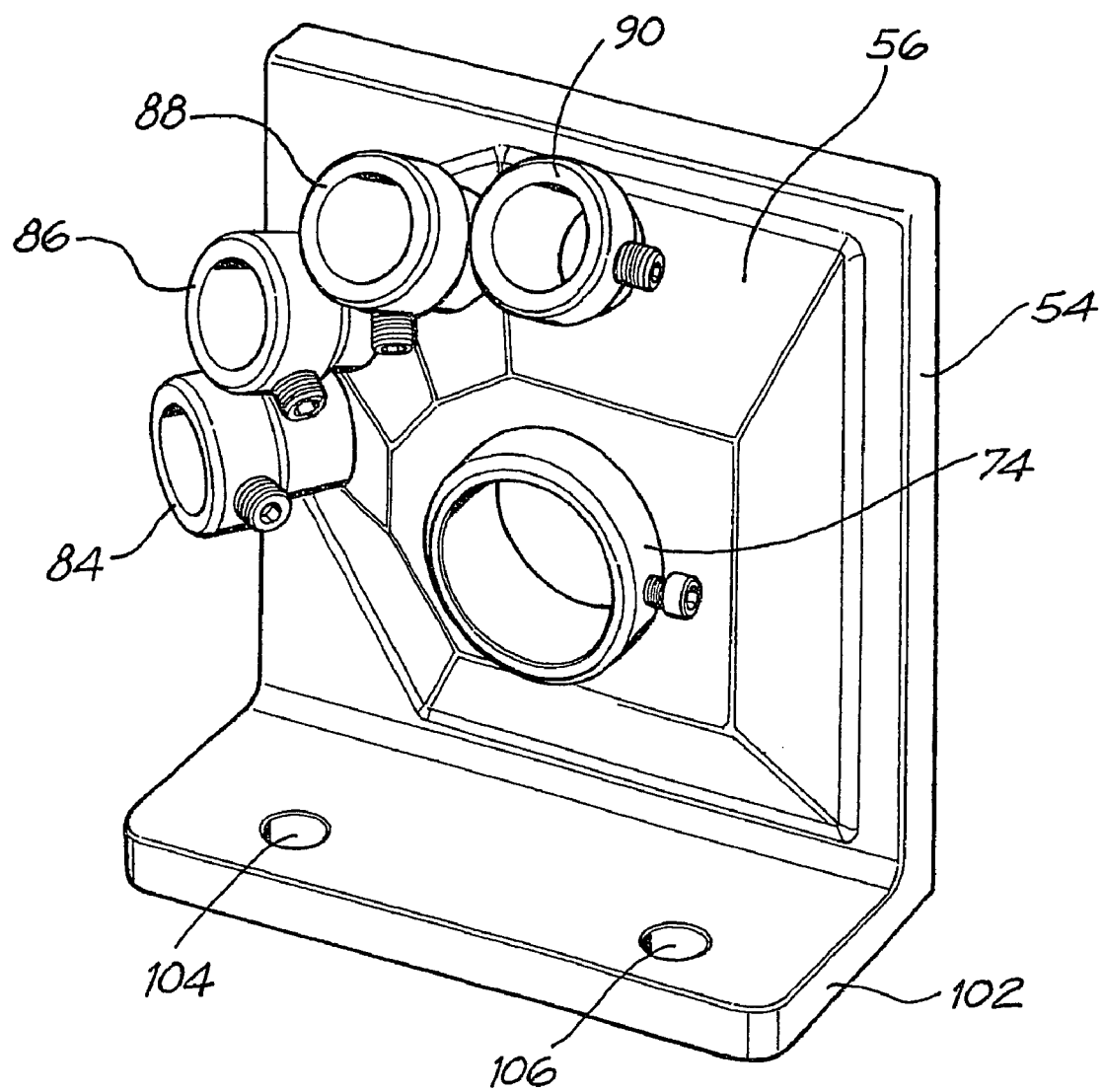
FIG. 4 is a perspective view of the apparatus of FIG. 2.

The apparatus shown in FIGS. 2 to 4 in accordance with the present invention is designed to be placed in the analyser in the region denoted by letter A in FIG. 1.

The apparatus 50 in accordance with the present invention and shown in FIG. 2 includes a chamber 52. The apparatus includes side walls 54, 56 and an upper end wall 58. A sliding dust tray 60 seals what would otherwise be an open bottom of chamber 52.

As it can be seen from FIG. 2, side wall 54 has an aperture 62 therein. Sample presentation means, in the form of a sliding sample holder 64, is adapted to be removably secured to side wall 54. When sliding sample holder 64 is in the position as shown in FIG. 2, aperture 62 in side wall 54 is effectively closed by the sliding sample holder 64. A seal is achieved between the sliding sample holder 64 and the side wall 54 by use of a gasket seal 66.

The sliding sample holder 64 is preferably machined out of a single piece of metal so that when the tray enters the side a round the end of the tray maintains the gas-tight integrity of the chamber.

Although the sample holder of FIG. 2 is shown as a sliding sample holder, it will be appreciated that any other form of sample holder that may be releasably secured to the apparatus may also be used in accordance with the present invention.

The sliding sample holder 64 includes a recess 68. Recess 68 receives and holds a sample 70 in place. The sample 70 may, for example, comprise a coal sample. It is preferred that the surface of sample 70 is relatively smooth.

The apparatus shown in FIG. 1 also includes a first window 72. First window 72 includes a lens. The lens position is adjustable to allow focusing of the laser beam onto the sample.

The laser used in conjunction with the apparatus 50 shown in the Figures is mounted in a separate laser holding means.

The apparatus 50 also includes a laser beam enclosing means 74 for guiding the laser beam from the laser into window 72. Laser beam guiding means 74 encloses the laser beam for safety purposes. The laser beam enclosing means 74 is best shown in FIG. 4. The laser beam enclosing means may suitably comprise a short tube having a set screw for securing the end of the laser in position.

One or more mirrors may also be used to direct the laser beam into the assembly.

The apparatus also includes a plurality of second windows 76, 78, 80, 82. Each of the second windows 76, 78, 80, 82 has a detector holding means 84, 86, 88, 90 associated therewith for holding detectors for detecting light emitted by the sample following a radiation of the sample with laser radiation. The detector holding means 84, 86, 88, 90 most clearly shown in FIG. 4. As with laser holding means 74, the detector holding means may comprise a short tube having a set screw for holding the detector therein. Other suitable arrangements for holding the detectors may also be used. A suitable detector may be an imaging lens and fibre optic conduit that transfers the emission to dector means 20, 22 and 24.

The plurality of second windows 76, 78, 80, 82 are most preferably formed as lenses to enable the light emitted by the sample to be focussed onto the detectors. Most suitably, the windows are formed by machining or casting holes into the assembly that perfectly align with the light emission from the sample and placing a lens in or over the hole.

It is also preferred that the plurality of fluorescence imaging devices or detectors (such as lens assemblies) are positioned within and releasably held by the detector holding means 84, 86, 88, 90 such that they are all exactly aligned to a desired point in the field of emitted light from the sample. Most preferably, the multiple fluorescence imaging devices are all exactly aligned to a point approximately 1 mm to 5 mm in front of the sample, most preferably about 2 mm in front of the sample. This is clearly shown in FIG. 3 where the incident laser beam 92 impinges on the sample and causes a spark 94 of emitted light to be emitted by the sample. The detectors held by the plurality of the detector holding means 84, 86, 88, 90 are all aligned and focussed such that they image the image region 96 that is typically positioned 1 mm to 5 mm in front of the sample, most preferably about 2 mm in front of the sample. In this regard, it has been found by the present inventors that maximum fluorescence response is obtained by focussing the laser onto the sample. However, it is preferred that the detectors for detecting light emitted by the sample are aligned to image the emitted light from a point positioned in front of the samples because the present inventors have found that the maximum emitted light signal is observed from a point just in front of the sample. Furthermore, imagining from a point in front of the sample reduces interfering background fluorescence and reduces noise, thereby maximising the performance of the analyser.

The apparatus 50 may further include gas inlet 98 and gas outlet 100. As shown in FIG. 1, gas inlet 98 and gas outlet 100 are positioned in an upper wall 58 of the apparatus. Although FIG. 2 appears to show only a single gas inlet or outlet, it will be appreciated that gas inlet 98 and gas outlet 100 in FIG. 2 are positioned such that they are in alignment with each other in side view. The gas inlet 98 and gas outlet 100 may be used for supplying buffer gas into and out of the chamber 50. Alternatively, a source of vacuum may be connected to one of the gas inlet 98 or gas outlet 100 (or to both thereof) if it is desired to apply a vacuum to the chamber.

As best shown in FIG. 4, the apparatus may also include a lateral extending flange 102 projecting from a bottom part of the apparatus. Laterally extending flange 102 may include holes 104, 106 that enable the flange to be securely bolted or otherwise affixed to a surface of the analyser. This ensures that the apparatus 50 is securely held in place on the analyser.

In FIG. 4, the gas inlet 98 and gas outlet 100 have been omitted for the sake of clarity.

Figure 5:
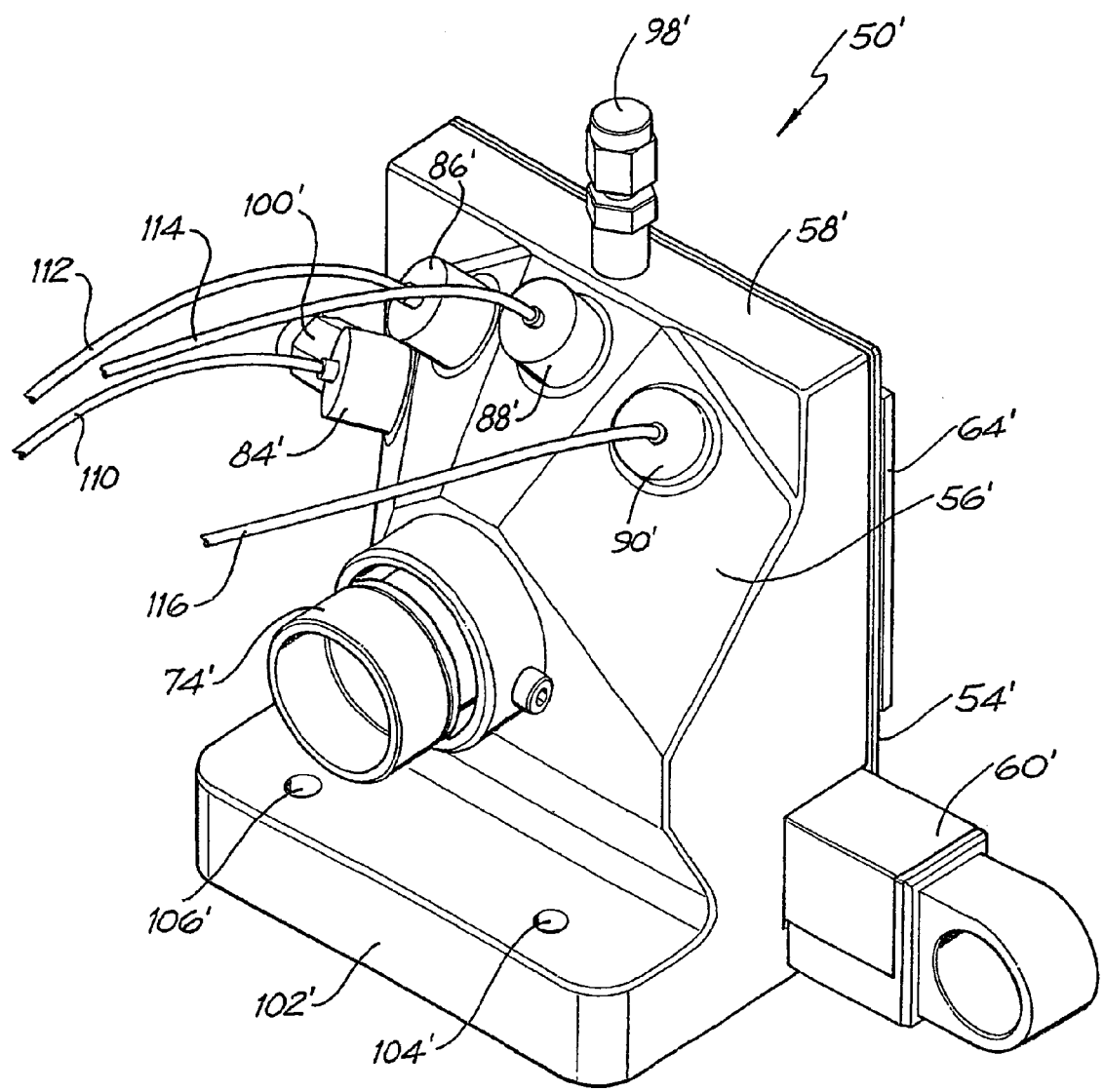
FIG. 5 is a perspective view of an apparatus in accordance with the present invention showing optical fibres connected thereto.
Figure 6:
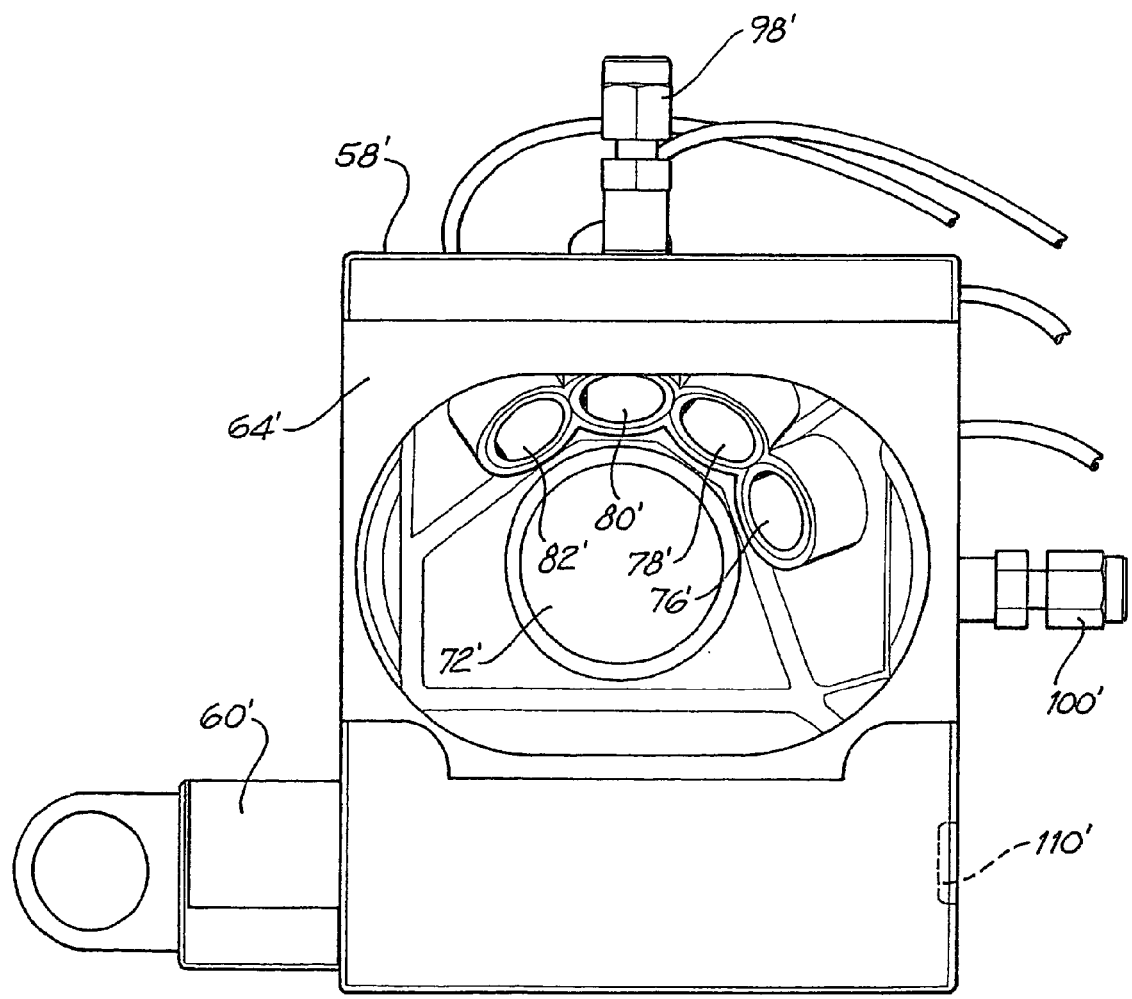
FIG. 6 is an end view of the apparatus of FIG. 5 with the sample holding means removed therefrom.

FIGS. 5 and 6 show another embodiment of the present invention. These features of FIGS. 5 and 6 that are essentially the same as the features of the embodiment shown in FIGS. 2–4 are denoted by the same reference numeral with a prime (') added. Those features need not be described further. In FIGS. 5 and 6, windows 76', 78', 80', 82', have fibre optic holders 84', 86', 88', 90', associated therewith to hold optic fibres 110, 112, 114, 116. The optic fibres transmit the emitted light gathered through windows 76', 78', 80', 82' to respective detectors.

Also shown schematically in FIG. 6 is safety interlock 110'. Safety interlock may comprise a switch or sensor that is responsive to the sliding dust tray 60'. When the dust tray' is in its fully closed position, switch or sensor 110' detects that the dust tray is fully closed. This disables an electrical interlock between switch or sensor 110' and the laser to thereby enable the laser to fire. When the dust tray 60' is not in its fully closed position, the sensor or switch 60' detects that fact and enables the electrical interlock, which prevents the laser from firing.

If desired, a similar safety interlock can be fitted to prevent the laser firing if the sliding sample holder 64 or 64' is not fully closed.

Those skilled in the art will appreciate that the present invention may be susceptible to variations and modifications other than those specifically described, it will be appreciated that the present invention extends to encompass all such variations and modifications that fall within its spirit and scope.

The invention claimed is:

1. An apparatus for presenting a sample of material for analysis by a laser-based analyser comprising a chamber, a first window for admitting laser radiation to the chamber, sample presentation means for presenting a sample such that said laser radiation can impinge upon the sample, and a plurality of second windows for receiving radiation emitted from the sample, said plurality of second windows adapted to pass radiation emitted from the sample to a plurality of detector means.

2. Apparatus as claimed in claim 1 wherein the chamber has one or more walls to define an interior thereof and said first window and said plurality of second windows are formed in said one or more walls.

3. Apparatus as claimed in claim 2 wherein the sample presentation means is removably secured to one or more walls of the chamber.

4. Apparatus as claimed in claim 3 wherein a wall of the chamber has an aperture therein and the sample presentation means positions the sample over, in or through the aperture such that laser radiation can pass through the first window and impinge upon the sample.

5. Apparatus as claimed in claim 4 wherein the sample presentation means forms a gas-tight seal when the sample presentation means is secured to the wall of the chamber.

6. Apparatus as claimed in any one of the preceding claims 1–2 wherein the first window includes a lens to enable laser radiation to be focussed onto the sample.

7. Apparatus as claimed in claim 6 wherein the position of the lens is adjustable to enable the focussing point for the laser radiation to be adjusted.

8. Apparatus as claimed in claim 7 wherein the lens is placed in an adjustable mount to enable focussing of the laser radiation.

9. Apparatus as claimed in any one of claims 1 to 2 wherein the sample presentation means is movable to allow the sample to be scanned across the laser beam during irradiation.

10. Apparatus as claimed in any one the preceding claims 1–2 wherein the plurality of second windows include lenses for collecting and focussing emitted light from the sample.

11. Apparatus as claimed in claim 10 wherein the plurality of second lenses are adjustable to enable their focal point to be adjusted.

12. Apparatus as claimed in claim 10 wherein the lenses collect light from a position that is from 1 mm to 5 mm in front of the sample.

13. Apparatus as claimed in any one of the preceding claims 1–2 further comprising a plurality of detector holding means for holding a plurality of detectors.

14. Apparatus as claimed in claim 13 wherein the detector holding means align the detectors such that the detectors detect emitted light from a position that is from 1 mm to 5 mm in front of the sample.

15. Apparatus as claimed in any one of the preceding claims 1–2 further comprising atmosphere control means for controlling the atmosphere inside the chamber.

16. Apparatus as claimed in claim 15 wherein the atmosphere control means comprises a gas inlet into the chamber to admitting gas into the chamber and a gas outlet from the chamber for removing gas from the chamber.

17. Apparatus as claimed in claim 15 wherein the atmosphere control means comprises a vacuum port for applying a vacuum to the chamber.

18. Apparatus as claimed in any one of the preceding claims 1–2 further comprising dust collection means for collecting dust from the sample.

19. Apparatus as claimed in claim 18 wherein the dust collection means comprises a slidable tray.

20. Apparatus as claimed in claim 18 wherein the dust collection means is in sealing engagement with the chamber when the dust collection means is in a closed position.

21. Apparatus as claimed in claim 3 further comprising safety interlock means for preventing firing of the laser if the sample presentation means and/or the dust collection means is not in a closed position.

22. Apparatus as claimed in claim 21 wherein the safety interlock means comprises electrical interlock means.

* * * * *